(12) United States Patent
Pradhan

(10) Patent No.: US 8,115,010 B2
(45) Date of Patent: Feb. 14, 2012

(54) FURANOSE DERIVATIVES

(75) Inventor: Braja Sundar Pradhan, Colchester (GB)

(73) Assignee: CBZ Chemicals Limited, Essex (GB)

( * ) Notice: Subject to any disclaimer, the term of this patent is extended or adjusted under 35 U.S.C. 154(b) by 0 days.

(21) Appl. No.: 12/664,455

(22) PCT Filed: Jun. 12, 2008

(86) PCT No.: PCT/GB2008/002008
§ 371 (c)(1), (2), (4) Date: Dec. 23, 2009

(87) PCT Pub. No.: WO2008/152386
PCT Pub. Date: Dec. 18, 2008

(65) Prior Publication Data
US 2010/0179331 A1    Jul. 15, 2010

Related U.S. Application Data

(60) Provisional application No. 60/943,357, filed on Jun. 12, 2007.

(30) Foreign Application Priority Data

Jun. 12, 2007   (GB) .................................. 0711250.1

(51) Int. Cl.
C07D 493/04    (2006.01)
C07D 207/36    (2006.01)
(52) U.S. Cl. ...................... 548/311.7; 548/537; 549/435
(58) Field of Classification Search .................. None
See application file for complete search history.

(56) References Cited

U.S. PATENT DOCUMENTS

| 5,003,080 | A | 3/1991 | Butler et al. |
| 5,273,995 | A | 12/1993 | Roth |
| 2004/0102511 | A1 | 5/2004 | Sattigeri et al. |
| 2006/0252816 | A1 | 11/2006 | Wang et al. |

FOREIGN PATENT DOCUMENTS
EP    0409281    1/1991

OTHER PUBLICATIONS

Hanriot et al., caplus an 1910:11642.*
Alais, Jocelyne et al., A Precursor to the .Beta.—Pyranosides of 3-amino-3, 6-Dideoxy-6-D-Mannose (Mycosamine), Carbohydrate Research, 1992, 203 (1), 79-87.
Gurjar, Mukund, K., et al., First Total Synthesis of Herbarumin III, Tetrahedron Letters, 2004, 45 (23), 4525-4526.
Hanaya, Tadashi, et al., Synthesis of 2,4-dideoxy-4-hydroxyphosphonoyl-D-erythro-and L-threo-pentofuranoses, Journal of the Chemical Society, Perkin Transactions 1: Organic and Bio-Organic Chemistry (1972-1999), 1992 (2), 295-301.
Takahashi, K. et al., "Efficient Method for a One-Carbon Homologation of Aldehydes and Benzophenone to Carboxylic Acid," Journal of Organic Chemistry, 1983, 48, 3566-3569.
Dinizo, S. et al., "A One-Carbon Homologation of Carbonyl Compounds to Carboxylic Acids, Esters, and Amides," Journal of the American Chemical Society, 1977, 99, 182-186.
International Search Report of International Application No. PCT/GB2008/002008 mailed on Aug. 14, 2008.
Broekhof, N.L.J.M, et al., "Enamine synthesis by the Horner-Wittig reaction," Tetrahedron Letters, vol. 20(26), 1979, pp. 2433-2436.

* cited by examiner

Primary Examiner — Sun Jae Loewe
(74) Attorney, Agent, or Firm — Pearl Cohen Zedek Latzer, LLP

(57) ABSTRACT

The invention relates to a process for preparing furanose derivatives, to furanose intermediates used in said process and to the use of said derivatives in the manufacture of atorvastatin.

(I)

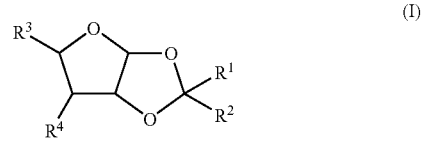

1 Claim, No Drawings

FURANOSE DERIVATIVES

CROSS-REFERENCE TO RELATED APPLICATIONS

This application is a National Phase Application of PCT International Application No. PCT/GB2008/002008, entitled "FURANOSE DERIVATIVES", International Filing Date Jun. 12, 2008, published on Dec. 18, 2008 as International Publication No. WO 2008/152386, which in turn claims priority from United Kingdom Patent Application No. 0711250.1, filed Jun. 12, 2007 and U.S. Provisional Patent Application No. 60/943,357, filed Jun. 12, 2007, all of which are incorporated herein by reference in their entirety.

FIELD OF THE INVENTION

The invention relates to a process for preparing furanose derivatives, to furanose intermediates used in said process and to the use of said derivatives in the manufacture of atorvastatin.

BACKGROUND OF THE INVENTION

Atorvastatin is a competitive inhibitor of the 3-hydroxy-3-methyl-glutaryl-coenzyme A (HMG-CoA) reductase, which is a key enzyme in the biosynthesis of cholesterol in humans. It has therefore proven to be a highly effective medication for the treatment of disorders such as hyperlipidemia and hypercholesterolemia which are conditions that are known risk factors for arteriosclerosis and coronary heart disease.

Atorvastatin is chemically (βR,δR)-2-(4-fluorophenyl)-β,δ-dihydroxy-5-(1-methylethyl)-3-phenyl-4-(phenylcarbamoyl)-1H-pyrrole-1-heptanoic acid and is marketed as its calcium salt under the brand name Lipitor™.

A number of processes and key intermediates for preparing Atorvastatin are known, for example U.S. Pat. No. 5,273,995 and US 2006/0252816.

SUMMARY OF THE INVENTION

According to a first aspect of the invention there is provided a use of a compound of formula (I):

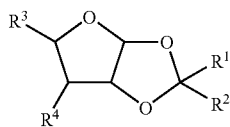

wherein
$R^1$ and $R^2$ independently represent hydrogen, halogen, $C_{1-6}$ alkyl, halo$C_{1-6}$ alkyl, $C_{2-6}$ alkenyl, $C_{2-6}$ alkynyl, $C_{1-6}$ alkanol, $C_{1-6}$ alkoxy, halo$C_{1-6}$ alkoxy, $C_{3-8}$ cycloalkyl or $C_{3-8}$ cycloalkenyl;
$R^3$ and $R^4$ independently represent hydrogen, halogen, $C_{1-6}$ alkyl optionally substituted by one or more (e.g. 1 to 3) $R^7$ groups, $C_{2-6}$ alkenyl optionally substituted by one or more (e.g. 1 to 3) $R^7$ groups, $C_{2-6}$ alkynyl, halo$C_{1-6}$ alkoxy, $C_{3-8}$ cycloalkyl, $C_{3-8}$ cycloalkenyl, —O$R^5$, —X-aryl, —X-heterocyclyl, —C($R^5$)=O, —C(=Y)—O—$R^5$,
aryl represents a carbocyclic ring;
heterocyclyl represents a heterocyclic ring optionally substituted by one or more (e.g. 1 to 3) $R^5$ substituents;
$R^5$ and $R^6$ independently represent a hydrogen or $C_{1-6}$ alkyl group;
$R^7$ represents a halogen, hydroxy, cyano, —COO$R^5$, —NO$_2$, —CONR$^5$R$^6$, —NR$^5$COOR$^6$ or —NR$^5$R$^6$ group;
X represents a bond, or a linker selected from —CO—(CH$_2$)$_m$—, —COO—, —(CH$_2$)$_p$—, —NR$^5$—(CH$_2$)$_m$—, —(CH$_2$)$_p$—NR$^5$—, —CONR$^5$—, —NR$^5$CO—, —SO$_2$NR$^5$—, —NR$^5$SO$_2$—, —NR$^5$CONR$^6$—, —NR$^5$CSNR$^6$—, —O—(CH$_2$)$_m$—, —(CH$_2$)$_p$—O—, S—, —SO— or —(CH$_2$)$_m$—SO$_2$—, —SO$_2$—O— or —O—SO$_2$—;
Y represents an O or an S atom;
m represents an integer from 0 to 4;
p represents an integer from 1 to 4;
in the preparation of atorvastatin.

The use of the compounds described herein as intermediates in the manufacture of atorvastatin provide a number of advantages. For example, the process is simple, efficient, and easy to operate as well as providing a good yield.

DETAILED DESCRIPTION OF THE INVENTION

The term '$C_{1-6}$ alkyl' as used herein as a group or a part of the group refers to a linear or branched saturated hydrocarbon group containing from 1 to 6 carbon atoms. Examples of such groups include methyl, ethyl, n-propyl, isopropyl, n-butyl, isobutyl, sec-butyl, tert butyl, n-pentyl, isopentyl, neopentyl or hexyl and the like.

The term '$C_{1-6}$ alkoxy' as used herein refers to an —O—$C_{1-6}$ alkyl group wherein $C_{1-6}$ alkyl is as defined herein. Examples of such groups include methoxy, ethoxy, propoxy, butoxy, pentoxy or hexoxy and the like.

The term '$C_{1-6}$ alkanol' as used herein refers to a $C_{1-6}$ alkyl group substituted by one or more hydroxy groups. Examples of such groups include methoxy, ethoxy, propoxy, butoxy, pentoxy or hexoxy and the like.

The term '$C_{3-8}$ cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

The term 'halogen' as used herein refers to a fluorine, chlorine, bromine or iodine atom.

The term 'halo$C_{1-6}$ alkyl' as used herein refers to a $C_{1-6}$ alkyl group as defined herein wherein at least one hydrogen atom is replaced with halogen. Examples of such groups include fluoroethyl, trifluoromethyl or trifluoroethyl and the like.

The term 'halo$C_{1-6}$ alkoxy' as used herein refers to a $C_{1-6}$ alkoxy group as herein defined wherein at least one hydrogen atom is replaced with halogen. Examples of such groups include difluoromethoxy or trifluoromethoxy and the like.

The term 'aryl' as used herein refers to a $C_{6-12}$ monocyclic or bicyclic hydrocarbon ring wherein at least one ring is aromatic. Examples of such groups include phenyl, naphthyl or tetrahydronaphthalenyl and the like.

The term 'heterocyclyl' as used herein refers to a 5-7 membered monocyclic aromatic ring, a fused 8-10 membered bicyclic aromatic ring, a 4-7 membered saturated or partially saturated monocyclic ring or a fused 8-12 membered saturated or partially saturated bicyclic ring containing 1 to 4 heteroatoms selected from oxygen, nitrogen and sulphur.

Examples of such monocyclic aromatic rings include thienyl, furyl, furazanyl, pyrrolyl, triazolyl, tetrazolyl, imidazolyl, oxazolyl, thiazolyl, oxadiazolyl, isothiazolyl, isoxazolyl, thiadiazolyl, pyranyl, pyrazolyl, pyrimidyl, pyridazinyl, pyrazinyl, pyridyl, triazinyl, tetrazinyl and the like.

Examples of such fused aromatic rings include quinolinyl, isoquinolinyl, quinazolinyl, quinoxalinyl, pteridinyl, cinnolinyl, phthalazinyl, naphthyridinyl, indolyl, isoindolyl, azaindolyl, indolizinyl, indazolyl, purinyl, pyrrolopyridinyl, furopyridinyl, benzofuranyl, isobenzofuranyl, benzothienyl, benzoimidazolyl, benzoxazolyl, benzoisoxazolyl, benzothiazolyl, benzoisothiazolyl, benzoxadiazolyl, benzothiadiazolyl and the like.

Examples of such saturated or partially saturated monocyclic rings include pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridinyl, tetrahydropyrimidinyl, tetrahydrothiophenyl, tetrahydrothiopyranyl, diazepanyl, azepanyl and the like.

Examples of such saturated or partially saturated bicyclic rings include indolinyl, isoindolinyl, benzopyranyl, quinuclidinyl, 2,3,4,5-tetrahydro-1H-3-benzazepine, tetrahydroisoquinolinyl and the like.

It will be appreciated that compounds of formula (I) may exist in a variety of differing optical configurations. For example, in one embodiment, the compound of formula (I) has the stereochemistry shown in the following compound of formula $(I)^a$:

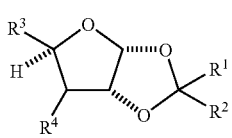

wherein $R^1$, $R^2$, $R^3$ and $R^4$ are as defined for compounds of formula (I). The stereochemistry demonstrated by compounds of formula $(I)^a$ provides the advantage of preparing the optimum diastereoisomer of atorvastatin which therefore results in the preparation of optically pure atorvastatin.

In one embodiment, $R^1$ and $R^2$ independently represent hydrogen or $C_{1-6}$ alkyl. In a further embodiment, $R^1$ and $R^2$ both represent $C_{1-6}$ alkyl (e.g. methyl). In a yet further embodiment, $R^1$ and $R^2$ both represent methyl.

In one embodiment, $R^3$ and $R^4$ do not both represent hydrogen.

In one embodiment, $R^3$ represents $C_{1-6}$ alkyl optionally substituted by one or more (e.g. 1 to 3) $R^7$ groups, $C_{2-6}$ alkenyl optionally substituted by one or more (e.g. 1 to 3) $R^7$ groups, —X-heterocyclyl or —C($R^5$)=O.

In one embodiment, $R^3$ represents $C_{1-6}$ alkyl optionally substituted by one or more $R^7$ groups (e.g. —CH$_2$—CH$_2$—NH$_2$, —CH$_2$—CH$_2$—NHCOOCH$_3$, —CH$_2$—CH$_2$—CONH$_2$, —CH$_2$—CH$_2$—NO$_2$, —CH$_2$—CH$_2$—COO—CH$_2$—CH$_3$, —CH(OH)—CH$_2$—NO, or —CH(OH)—CH$_2$OH).

In one embodiment, $R^3$ represents $C_{2-6}$ alkenyl optionally substituted by one or more $R^7$ groups (e.g. —CH=CH—COO—CH$_2$—CH$_3$ or —CH=CH—NO$_2$).

In one embodiment, $R^3$ represents —X-heterocyclyl optionally substituted by one or more $C_{1-6}$ alkyl groups, e.g. a group of formula (i):

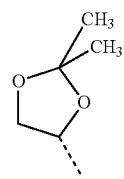

In one embodiment, $R^3$ represents —C($R^5$)=O (e.g. —C(H)=O.

In one embodiment, $R^4$ represents hydrogen, —OR$^5$, —X-heterocyclyl or —C(=Y)—O—R$^5$.

In one embodiment, $R^4$ represents hydrogen.
In one embodiment, $R^4$ represents —OR$^5$ (e.g. —OH).
In one embodiment, $R^4$ represents —X-heterocyclyl (e.g. —O—SO$_2$-imidazole). In a further embodiment, $R^4$ represents a group of formula (ii):

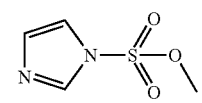

In one embodiment, $R^4$ represents —C(=Y)—O—R$^5$ (e.g. —C(=S)—O—CH$_3$).

According to a second aspect of the invention, there is provided a process for preparing a compound of formula (II):

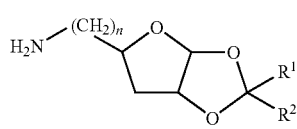

wherein $R^1$ and $R^2$ are as defined for compounds of formula (I) and n represents an integer from 1 to 4;
which comprises:
(a) deprotecting a compound of formula (III):

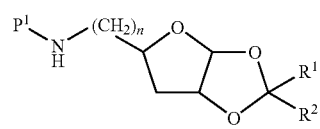

wherein $R^1$, $R^2$ and n are as defined for compounds of formula (II) and $P^1$ represents a suitable protecting group, such as carbobenzyloxy (cbz), t-butyloxycarbonyl (BOC), 9-fluorenylmethyloxycarbonyl (fmoc), benzyl, p-methoxyphenyl or an acetate (e.g. —COOCH$_3$) group; or
(b) hydrogenation of a compound of formula (IV):

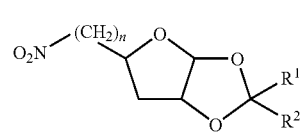

wherein $R^1$, $R^2$ and n are as defined for compounds of formula (II).

Step (a) typically comprises a hydrolysis reaction in the presence of a suitable base, such as sodium hydroxide.

Step (b) typically comprises a hydrogenation reaction, e.g. reaction of compound of formula (IV) with hydrogen in the presence of a suitable catalyst, such as Raney nickel.

In one embodiment, n represents an integer from 1-3. In a further embodiment, n represents 2.

Compounds of formula (III) wherein n represents 2 and $P^1$ represents —COOCH$_3$ may be prepared in accordance with the following Scheme 1:

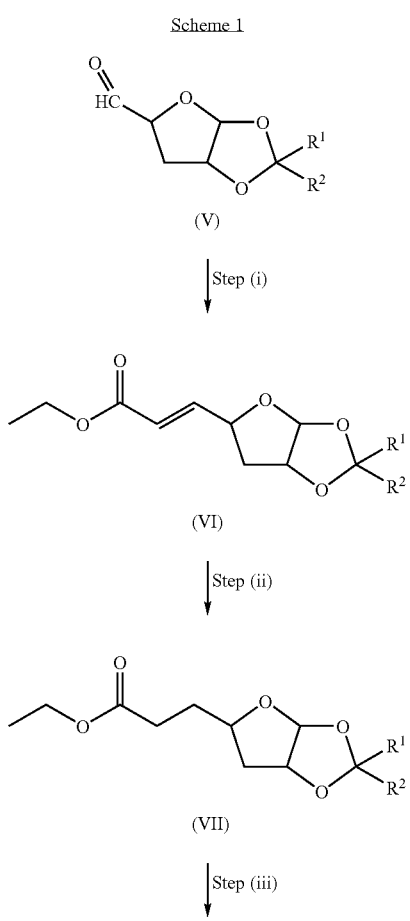

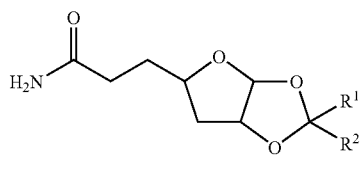

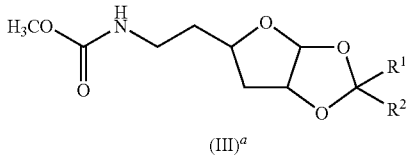

wherein $R^1$ and $R^2$ are as defined above for compounds of formula (II).

Step (i) typically comprises a Wittig reaction by condensing a compound of formula (V) with a Wittig reagent in the presence of a suitable base in a suitable solvent to afford a compound of formula (VI). In one embodiment, the Wittig reagent is triethylphosphonoacetate and the solvent is 1,2-dimethoxyethane.

Step (ii) typically comprises reacting the compound of formula (VI) with hydrogen in the presence of a suitable catalyst to afford a compound of formula (VII). In one embodiment, the catalyst is Raney nickel and the solvent is ethanol.

Step (iii) typically comprises reacting the compound of formula (VII) with a suitable amine, such as ammonia, to give a compound of formula (VIII).

Step (iv) typically comprises a Hofmann Rearrangement reaction by reacting the compound of formula (VIII) with a suitable halogen atom, such as chlorine or bromine (e.g. bromine) and a suitable base (e.g. sodium methoxide) in the presence of a suitable solvent (e.g. methanol), followed by hydrolysis, to afford a compound of formula (III)$^a$. In one embodiment, the Hofmann Rearrangement reaction may additionally comprise an acetate salt, typically mercuric acetate, to afford a compound of formula (III)$^a$.

Compounds of formula (IV) wherein n represents 2 may be prepared in accordance with the following Scheme 2:

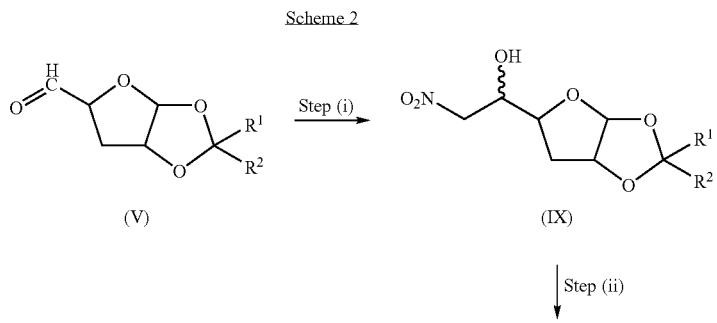

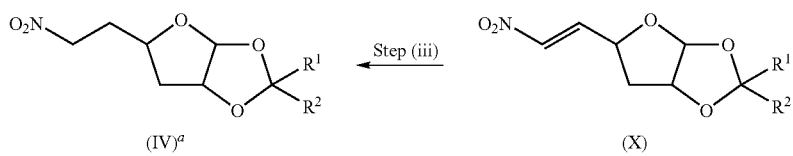

wherein $R^1$ and $R^2$ are as defined above for compounds of formula (II).

Step (i) typically comprises a Henry (Nitroaldol) reaction by reacting a compound of formula (V) with a suitable nitroalkane (e.g. nitromethane) in the presence of a suitable base (e.g. sodium methoxide) in a suitable solvent (e.g. anhydrous methanol) to afford a compound of formula (IX). In one embodiment, the nitroalkane is nitromethane, the base is sodium methoxide and the solvent is anhydrous methanol.

Step (ii) typically comprises reacting the compound of formula (IX) under eliminating conditions to afford a compound of formula (X). In one embodiment, the eliminating conditions comprise reacting the compound of formula (IX) with a dehydrating agent to yield a compound of formula (X).

Typical dehydrating agents include acid anhydrides and dicyclohexylcarbodiimide. In another embodiment, the nitroalcohol of formula (IX) is reacted with an anhydride, typically acetic anhydride, to form a nitroester. This nitroester may then be reacted with a mild base, for example acetate salts, e.g. sodium acetate, to form the compound of formula (X).

Step (iii) typically comprises reacting the compound of formula (X) with a reducing agent in a suitable solvent to afford a compound of formula $(IV)^a$. In one embodiment, the reducing agent is sodium borohydride and the solvent is methanol.

Compounds of formula (V) may be prepared in accordance with the following Scheme 3:

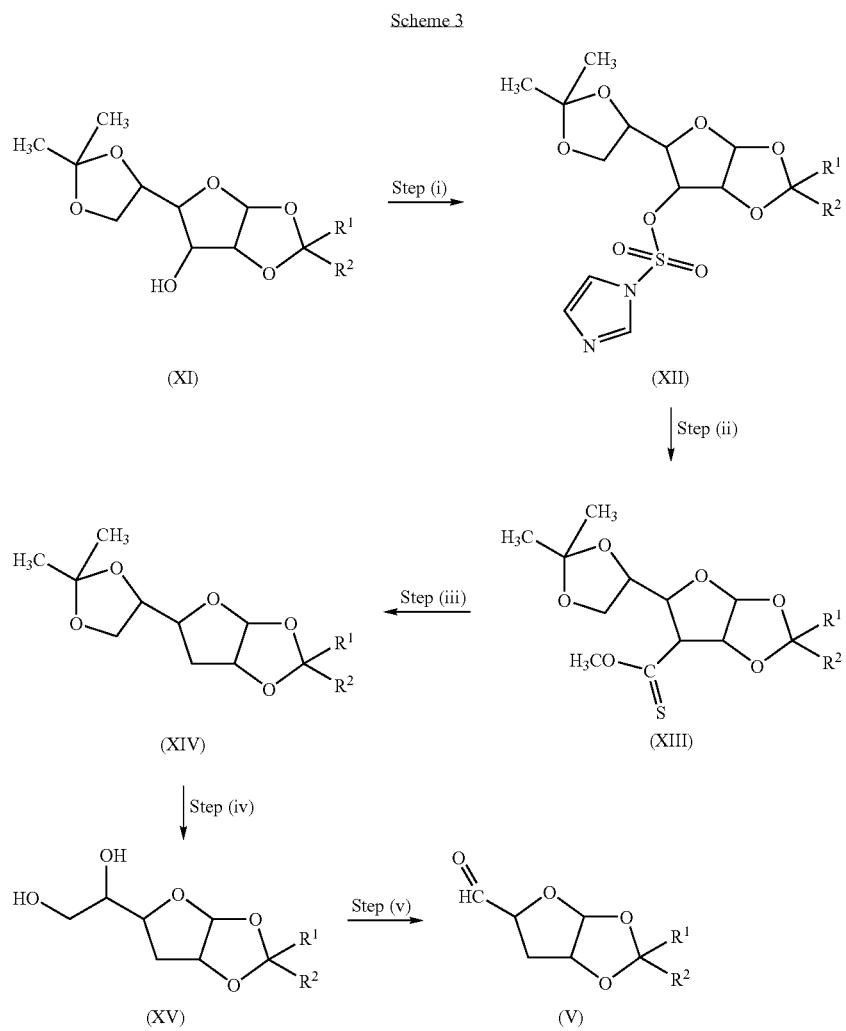

wherein R¹ and R² are as defined above for compounds of formula (II).

Step (i) typically comprises reaction of a compound of formula (XI) with imidazole in the presence of sulfuryl chloride and a suitable solvent (e.g. dichloromethane) to yield a compound of formula (XII).

Step (ii) typically comprises reaction of a compound of formula (XII) with potassium thioacetate in the presence of a suitable solvent (e.g. dimethylformamide) to yield a compound of formula (XIII).

Step (iii) typically comprises a hydrogenation reaction in the presence of a suitable catalyst (e.g. Raney nickel) in the presence of a suitable solvent (e.g. methanol) to yield a compound of formula (XIV).

Step (iv) typically comprises reacting a compound of formula (XIV) in the presence of a suitable acid (e.g. aqueous hydrochloric acid) to yield a compound of formula (XV).

Step (v) typically comprises an oxidisation reaction by reacting a compound of formula (XV) with an oxidising agent (e.g. sodium periodate) in a suitable solvent (e.g. ethanol) to yield a compound of formula (V).

Compounds of formula (XI) are either known or may be prepared in accordance with known procedures (e.g. from D-glucose).

According to a further aspect of the invention, there is provided a compound selected from:

1,2:5,6-Di-O-isopropylidene-3-O-(imidazole-1-sulfonyl)-α-D-glucofuranose (E1)

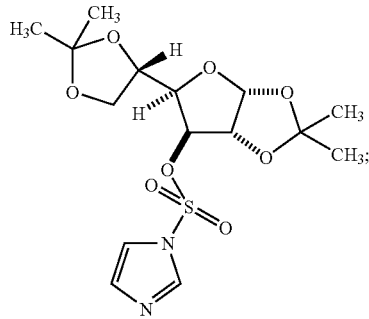

3-S-Acetyl-1,2:5,6-di-O-isopropylidene-3-thio-α-D-allofuranose (E2)

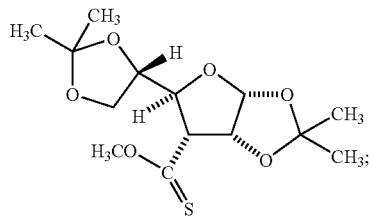

1,2-O-Isopropylidene-α-D-erythro-pentodialdo-1,4-furanose (E5)

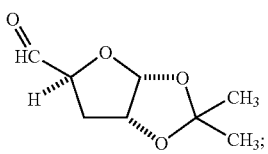

Ethyl 3,5,6-trideoxy-1,2-O-isopropylidene-α-D-erythro-hept-5-enoato-1,4-furanose (E6)

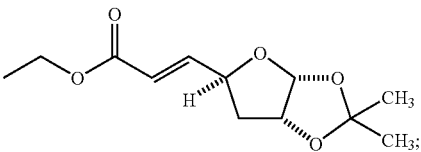

Ethyl 3,5,6-trideoxy-1,2-O-isopropylidene-α-D-erythro-heptanoato-1,4-furanose (E7)

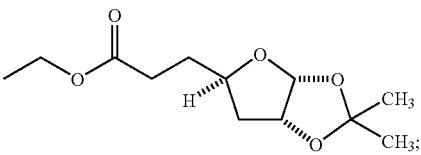

3,5,6-Trideoxy-1,2-O-isopropylidene-α-D-erythro-heptamido-1,4-furanose (E8)

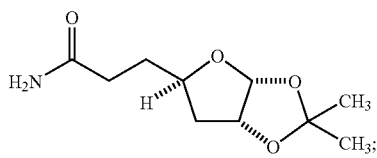

3,5,6-Trideoxy-1,2-O-isopropylidene-6-methoxycarbonylamido-α-D-erythro-hexofuranose (E9)

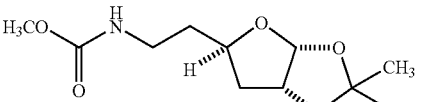

3,5,6-Trideoxy-1,2-O-isopropylidene-6-amino-α-D-erythro-hexofuranose (E10)

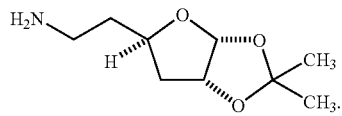

and

According to a further aspect of the invention, there is provided a process for preparing atorvastatin which comprises the following steps:

(a) reaction of a compound of formula (II)$^a$

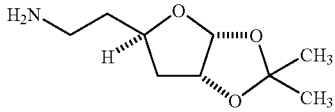

with a compound of formula (XVI):

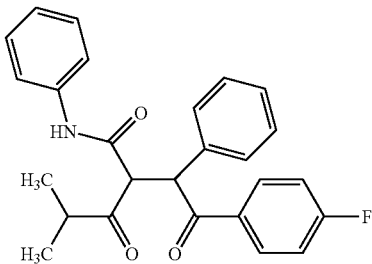

(XVI)

to yield a compound of formula (XVII)

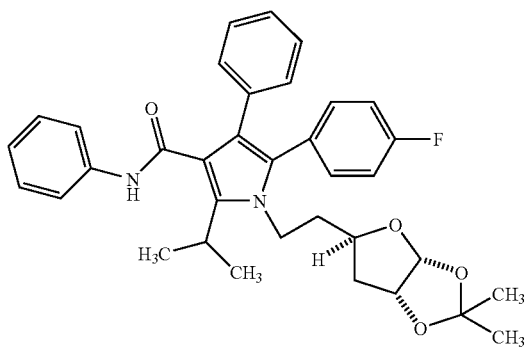

(XVII)

(b) reaction of a compound of formula (XVII) as defined above to yield a compound of formula (XVIII)

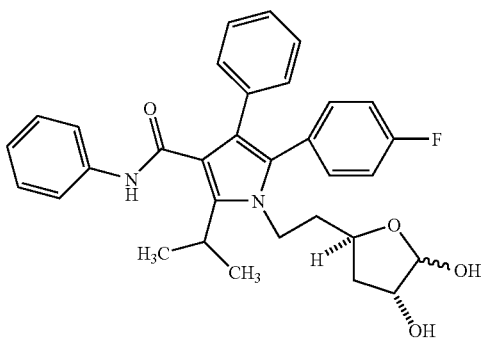

(XVIII)

(c) reaction of a compound of formula (XVIII) as defined above to yield atorvastatin.

Step (a) typically comprises reaction in a suitable solvent (e.g. tetrahydrofuran and n-heptane) and suitable agents (e.g. pivalic acid and toluene) at a suitable temperature (e.g. room temperature).

Step (b) typically comprises treatment of a compound of formula (XVII) with aqueous trifluoroacetic acid.

Step (c) typically comprises a Wittig reaction involving one-carbon homologation. Such a reaction will be readily apparent to the skilled person and is described in Journal of American Chemical Society, (1977), 99, 182; Journal of Organic Chemistry, (1983), 48, 3566; and Tetrahedron Letters, (1979), 26, 2433.

Compounds of formula (II)$^a$ may be prepared in accordance with procedures described herein.

Compounds of formula (XVI) are known, for example, from compounds of formula (XVII) in U.S. Pat. No. 5,003,080.

The invention will now be illustrated by the following non-limiting examples:

EXAMPLES

Example 1

1,2:5,6-Di-O-isopropylidene-3-O-(imidazole-1-sulfonyl)-α-D-glucofuranose (E1)

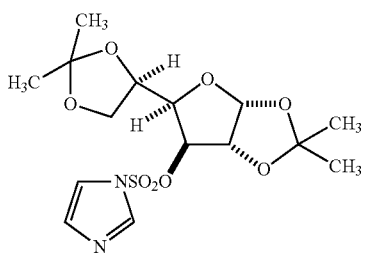

To a stirred solution of 1,2:5,6-di-O-isopropylidene-α-D-glucofuranose (250 g, 961.54 mmol) in anhydrous dichloromethane (3.59 it) imidazole (440 g, 646 mmole) was added at 0 to −5° C. over a period of 0.5 h. The reaction mixture was stirred for 1 h at this temperature and then a solution of sulfuryl chloride (149 ml) in dichloromethane (20 ml) was added drop wise to the mixture. After 5 h at 0 to −5° C., the reaction mixture was allowed to warm to room temperature and stirred at this temperature until the reaction is completed as indicated by thin layer chromatography (TLC).

The precipitated salt was filtered and the filtrate was washed with water (3×1000 ml). The organic layer was then washed successively with 10% aqueous hydrochloric acid (10×1000 ml), water (1×1000 ml), saturated sodium bicarbonate solution (2×1000 ml), water (1×1000 ml) and finally with brine (2×1000 ml). The organic layer was dried over sodium sulfate and concentrated under reduced pressure to give the title product (E1) as a solid; yield 320 g, yield 95%.

Example 2

3-S-ThioAcetyl-1,2:5,6-di-O-isopropylidene-3-thio-α-D-allofuranose (E2)

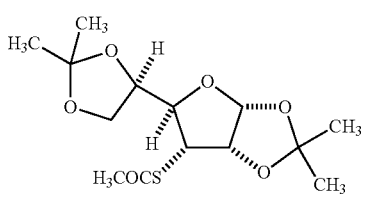

Potassium thioacetate (7.3 g, 63.93 mmol) was added to a stirred solution of 1,2:5,6-di-O-isopropylidene-3-O-(imidazole-1-sulfonyl)-α-D-glucofuranose E1 (10.0 g, 25.64 mmol) of in dimethylformamide (25 ml) and the reaction mixture was heated at 75-85° C. for 5 h.

After completion of the reaction as indicated by TLC, the reaction mixture was diluted with ethyl acetate (50 ml) and water (25 ml). Charcoal (25 g) was then added and the reaction was maintained at 55-60° C. for 0.5 h and then filtered. The filtrate was washed with water (10×25 ml) and with brine (2×25 ml), dried over sodium sulfate and concentrated under reduced pressure to give the title compound E2; yield: 7.5 g, 84% which was subjected to the following step without further purification.

Example 3

3-Deoxy-1,2:5,6-di-O-isopropylidene-α-D-ribo-hexofuranose (E3)

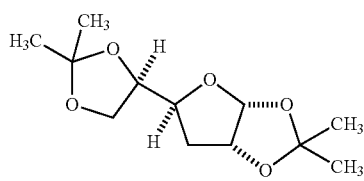

The crude reaction mixture obtained by the procedure described in Example 2 containing 3-S-thioacetyl-1,2:5,6-di-O-isopropylidene-3-thio-α-D-allofuranose E2 (7.5 g, 23.58 mmole) was dissolved in methanol and added to a slurry of freshly prepared Raney Nickel (prepared from nickel-aluminium alloy, 60 g) in 100 ml of methanol. The reaction mixture was stirred at room temperature for 15 h and filtered. The filtrate was reduced under reduced pressure to give the title product E3; yield: 5 g, 88%, which was subjected to the following step without further purification.

Example 4

3-Deoxy-1,2-O-isopropylidene-α-D-ribo-hexofuranose (E4)

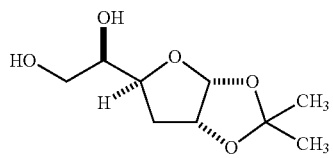

A slurry of 3-deoxy-1,2:5,6-di-O-isopropylidene-α-D-ribo-hexofuranose E3 (5.0 g, 20.49 mmol) in aqueous hydrochloric acid (200 ml, 0.01N) was stirred at room temperature for 12 h. After the completion of reaction as indicated by TLC, the reaction mixture was neutralized by adding sodium bicarbonate and extracted with n-hexane (1×100 ml) to remove non-polar organic impurities. The aqueous reaction mixture was then extracted with ethyl acetate (5×10 ml). The organic layer was dried over sodium sulfate and concentrated under reduced pressure at 50° C. to give the title compound (E4); yield: 4 g, 95.69%.

Example 5

1,2-O-Isopropylidene-α-D-erythro-pentodialdo-1,4-furanose (E5)

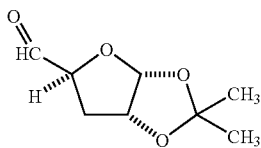

A solution of sodium periodate (8.4 g, 39.27 mmol) in water (64 ml) was added drop wise to a cooled solution of 3 deoxy-1,2-O-isopropylidene-α-D-ribo-hexofuranose E4 (8.0 g, 39.22 mmol) in ethanol (64 ml) at 0-10° C. The reaction mixture was allowed to warm to room temperature and stirred for 1 h when the reaction completed as indicated by TLC. The precipitated mass was filtered and the filtrate was concentrated under reduced pressure at 75° C. to a thick syrup. Ethyl Acetate (100 ml) was then added and the mixture was stirred at room temperature for 15 minutes until the thick syrup dissolved to give a homogenous solution. The solution was washed with brine (2×25 ml), dried over sodium sulfate and filtered. The filtrate was concentrated under reduced pressure to give the title compound (E5); yield: 6.5 g, 96% which was subjected to the following step without further purification.

Example 6

Ethyl 3,5,6-trideoxy-1,2-O-isopropylidene-α-D-erythro-hept-5-enoato-1,4-furanose (E6)

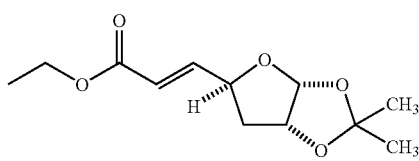

Triethylphosphonoacetate (11 g, 49.06 mmol) 1,2-dimethoxyethane (16.5 ml) was added under an atmosphere of nitrogen to a slurry of sodium hydride (1.8 g, 45 mmol; 60% dispersion In mineral oil) in 1,2-dimethoxyethane (16.5 ml) at 0-5° C. After 0.5 h at 0-5° C. a solution of 1,2-O-isopropylidene-α-D-erythro-pentodialdo-1,4-furanose E5 (6.5 g, 37.79 mmol) in 1,2-dimethoxyethane (33 ml) was added drop wise to the reaction mixture under an atmosphere of nitrogen at 0-5° C. The reaction mixture was allowed to warm to room temperature and stirred at this temperature for 1 h when the TLC of the reaction mixture indicated the completion of the reaction. The reaction was quenched by adding water (50 ml). After 15 minutes, ethyl acetate (150 ml) was added to the reaction mixture to facilitate the separation of layers. The organic layer was washed successively with water (1×50 ml), brine (1×50 ml), dried over sodium sulphate and filtered. The filtrate was concentrated under reduced pressure at 75° C. to give the title compound (E6) as a thick syrup; yield: 9 g, 94%.

Example 7

Ethyl 3,5,6-trideoxy-1,2-O-isopropylidene-α-D-erythro-heptanoato-1,4-furanose (E7)

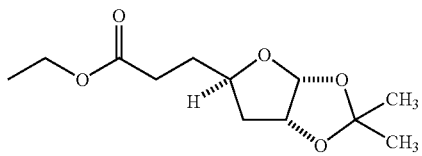

A slurry of freshly prepared Raney nickel (18 g of nickel-aluminium alloy gave approximately 9.0 g of Raney nickel) in ethanol (45 ml) was added to ethyl 3,5,6-trideoxy-1,2-O-isopropylidene-α-D-erythro-hept-5-enoato-1,4-furanose E6 (9 g, 37.19 mmole) dissolved in ethanol (45 ml). The reaction mixture was stirred under an atmosphere of hydrogen at 50 psi at room temperature until the uptake of hydrogen stopped and the reaction completed as indicated by TLC. The reaction mixture was then filtered and the Raney nickel residue was washed with ethanol (18 ml). The combined filtrate was concentrated under reduced pressure to give the title compound E7; yield: 9.0 g, 99%.

Example 8

3,5,6-Trideoxy-1,2-O-isopropylidene-α-D-erythro-heptamido-1,4-furanose (E8)

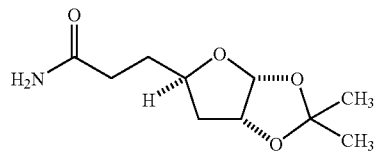

An aqueous solution of ammonia (90 ml) was added to ethyl 3,5,6-trideoxy-1,2-O-isopropylidene-α-D-erythro-heptanoato-1,4-furanose E7 (9 g, 36.89 mmole and the reaction mixture was stirred at room temperature for 15 h when the reaction completed as indicated by TLC.

The reaction mixture was then extracted with ethyl acetate (4×100 ml). The organic layer was dried over sodium sulfate and then filtered. The filtrate was concentrated under reduced pressure to give the title compound E8; yield: 6.8 g, 85.7%).

Example 9

3,5,6-Trideoxy-1,2-O-isopropylidene-6-methoxycarbonylamido-α-D-erythro-hexofuranose (E9)

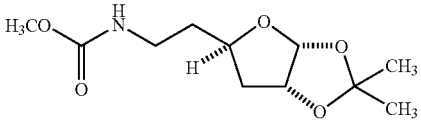

Bromine (4.64 g, 29.03 mmole) was added drop wise at −45° C. to a cold solution of freshly prepared sodium methoxide (prepared from 2.1 g of sodium) in methanol (50 ml). The reaction mixture was maintained at −45° C. until the colour of bromine disappeared. A solution of 3,5,6-trideoxy-1,2-O-isopropylidene-α-D-erythro-heptamido-1,4-furanose E8 (6.5 g, 30.23 mmole) in dioxane (32.5 ml) and methanol (19.5 ml) was added drop wise to the reaction mixture at −45° C. The reaction mixture was then allowed to warm to the room temperature and then heated slowly until the bath temperature attained 55-60° C. After 1 h at 55-60° C., the reaction mixture was neutralized with acetic acid and concentrated under reduced pressure below 50° C. to remove 1,4-dioxane and methanol. Ethyl acetate (150 ml) was added to the mixture and extracted with water (1×50 ml). The organic layer was washed with saturated sodium bicarbonate solution (3×25 ml), water (3×50 ml), brine (1×50 ml), dried over sodium sulfate and filtered. The filtrate was concentrated under reduced pressure to give the rearranged title compound E9; yield: 4.5 g, 61%.

Example 10

3,5,6-Trideoxy-1,2-O-isopropylidene-6-amino-α-D-erythro-hexofuranose (E10)

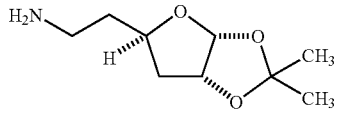

Sodium hydroxide (35 ml., 1N) was added to 3,5,6-trideoxy-1,2-O-isopropylidene-6-methoxycarbonylamido-α-D-erythro-hexofuranose E9 (3.5 g, 14.29 mmole) at room temperature. The mixture was then heated slowly until the bath temperature attained 80-85° C. After 10 h at 80-85° C., the reaction mixture was cool down to room temperature and then extracted with ethyl acetate (2×100 ml, 3×50 ml). The combined ethyl acetate layers was dried over sodium sulfate and filtered. The filtrate was concentrated under reduced pressure to give the title compound E10; yield: 2.0 g, 74%).

Example 11

3,5-Dideoxy-1,2-O-isopropylidene-6-[5-(4-fluorophenyl)-2-(1-methylethyl)-N,4-diphenyl-1H-pyrrole-3-carboxamide]-α-D-etythro-hexofuranose (E11)

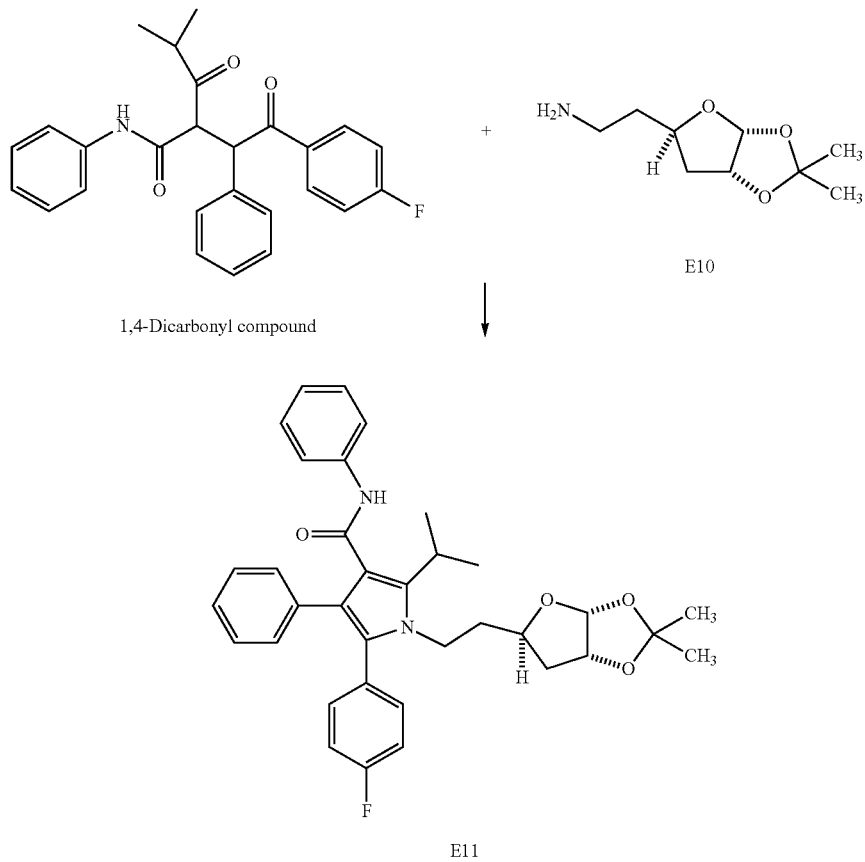

To a solution of 3,5,6-trideoxy-1,2-O-isopropylidene-6-amino-α-D-erythro-hexofuranose (E10) (0.6 g, 3.21 mmol) in tetrahydrofuran (5 ml) was added at room temperature 1,4-dicarbonyl compound (Compound XVII in U.S. Pat. No. 5,003,080) (1.0 g, 2.5 mmole), pivalic acid (0.32 g, 3.13 mmol), toluene (5 ml) and n-heptane (20 ml). The reaction mixture was then heated slowly to reflux with azeotropic removal of water. After completion of the reaction as indicated by TLC (usually takes 24 h-30 h of reflux), the reaction mixture was allowed to cool down to room temperature. Ethylacetate (50 ml) and water (25 ml) were added to the reaction mixture to facilitate separation of layers. The organic layer was extracted with sodium hydrogencarbonate solution (3×50 ml), water (3×50 ml) and finally with brine (1×50 ml); dried over sodium sulphate and filtered. The filtrate was concentrated under reduced pressure to give the title compound E11; yield: 1.5 g, 85%.

Example 12

3,5-Dideoxy-6-[5-(4-fluorophenyl)-2-(1-methylethyl)-N,4-diphenyl-1H-pyrrole-3-carboxamide]-(α and β)-D-erythro-hexofuranose (E12)

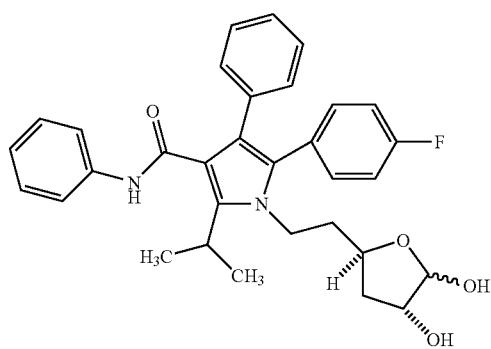

An aqueous solution of trifluoroacetic acid (2 ml), (TFA: Water, 3:1) was added at 0-10° C. to 3,5-dideoxy-1,2-O- isopropylidene-6-[5-(4-fluorophenyl)-2-(1-methylethyl)-N,4-diphenyl-1H-pyrrole-3-carboxamide]-α-D-erythro-hexofuranose (E11). On completion of the reaction as indicated by TLC (4 h at 0-10° C.), the reaction mixture was diluted with cold water and then neutralized with solid sodium hydrogen carbonate. The precipitated solid was filtered, slurried with n-hexane and then filtered. The residue was dissolved in ethyl acetate and was extracted with water (2×25 ml) and finally with brine (1×25 ml); dried over sodium sulphate and filtered. The filtrate was concentrated under reduced pressure to give the title compound E12; yield: (0.4 g, 43%).

Example 13

[R—(R*,R*)]-2-(4-fluorophenyl)-β,δ-dihydroxy-5-(1-methylethyl)-3-phenyl-4-(phenylcarbamoyl)-1H-pyrrole-1-heptanoic acid (E13)

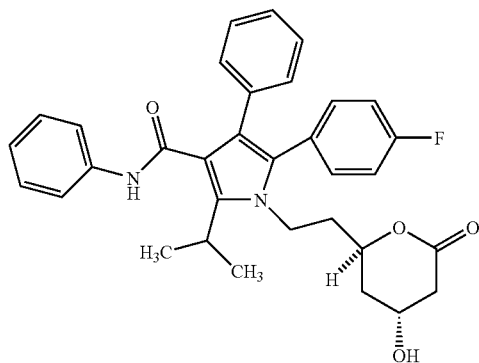

The title compound (atorvastatin lactone; E13) may be prepared by subjecting 3,5-dideoxy-6-[5-(4-fluorophenyl)-2-(1-methylethyl)-N,4-diphenyl-1H-pyrrole-3-carboxamide]-(α and β)-D-erythro-hexofuranose (in E12) to a Wittig reaction involving one-carbon homologation. Such a reaction will be readily apparent to the skilled person and is described in Journal of American Chemical Society, (1977), 99, 182; Journal of Organic Chemistry, (1983), 48, 3566; and Tetrahedron Letters, (1979), 26, 2433.

The invention claimed is:

1. A process for preparing atorvastatin which comprises the following steps:

(a) reacting of a compound of formula (II)$^a$ (II)$^a$

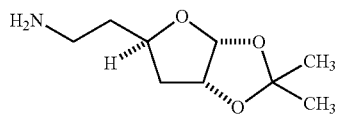

with a compound of formula (XVI):

(XVI)

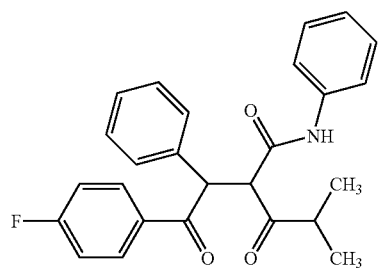

to yield a compound of formula (XVII)

(XVII)

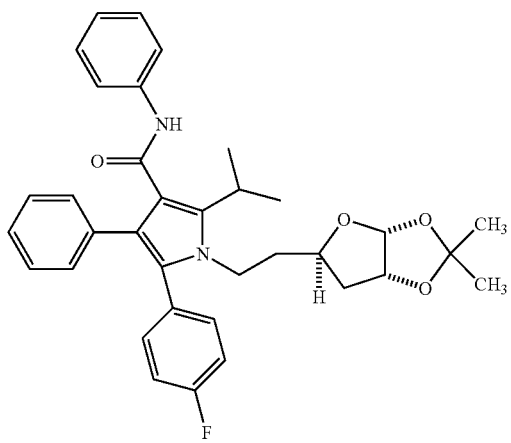

(b) reacting of a compound of formula (XVII) to yield a compound of formula (XVIII)

(XVIII)

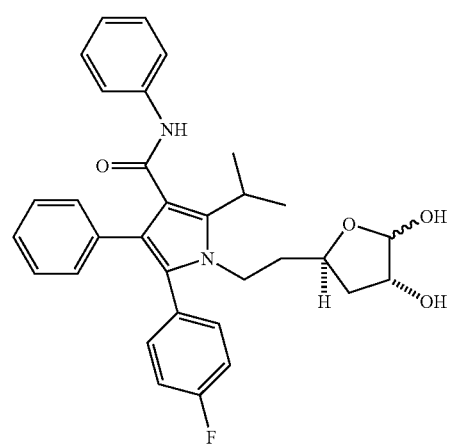

(c) reacting of a compound of formula (XVIII) to yield atorvastatin.

* * * * *